United States Patent [19]

Tanahashi et al.

[11] Patent Number: 4,649,364

[45] Date of Patent: Mar. 10, 1987

[54] BIFUNCTIONAL ENVIRONMENT SENSOR

[75] Inventors: Maki Tanahashi, Kyoto; Sumio Horiike, Ohtsu; Hiroyuki Nakano, Osaka, all of Japan

[73] Assignee: Omron Tateisi Electronics Co., Kyoto, Japan

[21] Appl. No.: 651,869

[22] Filed: Sep. 18, 1984

[30] Foreign Application Priority Data

Sep. 20, 1983 [JP] Japan .................. 58-175042

[51] Int. Cl.$^4$ .............................. H01C 7/00
[52] U.S. Cl. .................. 338/14; 338/22 R; 338/35
[58] Field of Search ............ 338/14, 34, 35, 22 R, 338/22 SD; 73/23, 25, 30, 29

[56] References Cited

U.S. PATENT DOCUMENTS 4,007,435 2/1977 Tien .................. 338/14 X
4,033,169 7/1977 Fujishiro et al. ........... 338/14 X

FOREIGN PATENT DOCUMENTS 53-25896 3/1978 Japan ..................... 338/14

Primary Examiner—E. A. Goldberg
Assistant Examiner—M. M. Lateef
Attorney, Agent, or Firm—Wegner & Bretschneider

[57] ABSTRACT

An environment sensor includes an insulating base board, a first electrode made of a material which can provide an electrical indication of the value of a first physical quantity and formed on the insulating base board, a second electrode formed of electrically conducting material and formed on the insulating base board, and a mass of metal oxide semiconductor material which can provide an electrical indication of the value of a second physical quantity, layered on the base board over the first and second electrodes. Thus, the first electrode by itself constitutes a sensor subsystem which can sense the value of the first physical quantity, which may preferably be temperature, while the first and second electrodes together with the mass of metal oxide semiconductor material constitute a sensor subsystem which can sense the value of the second physical quantity, which may preferably be humidity.

11 Claims, 4 Drawing Figures

BIFUNCTIONAL ENVIRONMENT SENSOR

BACKGROUND OF THE INVENTION

The present invention relates to a bifunctional environment sensor, and in particular to such a bifunctional environment sensor which can detect the values of two different physical quantities at the same time.

Conventionally, for sensing the values of various parameters of the external environment such as temperature, humidity, gas concentration, smog concentration, smoke concentration, and so on, methods are known for making use of electroconductivity in metal oxides and resins and so on, and methods using semiconductor material and so on are known. Devices utilizing such principles are also known; however, such devices have always only been able to detect the value of one parameter of the external environment, and no device has been proposed which can detect the values of two environmental parameters at the same time, such as the values of any two of temperature, humidity, gas concentration, smog concentration, and smoke concentration. In other words, one sensing device has hitherto been capable only of detecting the value of one physical quantity, and in order to detect the values of two different physical quantities two sensing devices having different properties have had to be used.

However, in the case of many such sensing devices for various parameters, and particularly in the case of humidity sensing devices for sensing relative humidity, sometimes they have temperature dependence, and accordingly it has been practiced to correct or to compensate the humidity value sensed by such a humidity sensing device according to the value of the output of another sensor for sensing the ambient temperature around said humidity sensing device, said temperature sensing device being placed adjacent to the humidity sensing device and as near to it as possible. However, this correction method leads to problems. For instance, if the base boards of the two sensor devices have different thermal conductivities, then the speed of response of the two sensor devices is different, and accurate correction of the humidity readings provided by the humidity detector according to the temperature readings provided by the temperature sensor cannot be performed. Therefore, accurate values of physical quantities cannot be practicably sensed in this way. Further, if two such separate sensor devices are used, then the combination cannot be made compact, and the cost thereof tends to be high.

SUMMARY OF THE INVENTION

Accordingly, it is the primary object of the present invention to provide an environment sensing device which is capable of sensing the values of two physical quantities at the same time.

It is a further object of the present invention to provide such an environment sensing device which is thus capable of sensing the values of two physical quantities, independently.

It is a further object of the present invention to provide such a bifunctional environment sensing device which has a high sensing accuracy.

It is a further object of the present invention to provide such a bifunctional environment sensing device which is suitable for measuring the value of a first physical quantity and also for measuring the value of a second physical quantity the value of which is used for correcting said measurement made of said value of said first physical quantity.

It is a further object of the present invention to provide such a bifunctional environment sensing device which in particular is capable of sensing the value of temperature along with the value of some other physical quantity.

It is a further object of the present invention to provide such a bifunctional environment sensing device which in particular is capable of sensing the value of temperature along with the value of relative humidity.

It is a further object of the present invention to provide such a bifunctional environment sensing device which is thus capable of sensing the value of temperature along with the value of relative humidity, and which provides an output temperature value which corresponds to the temperature of the humidity sensor substantially exactly, so that good temperature correction may be made for the output value provided by said humidity sensor.

It is a yet further object of the present invention to provide such a bifunctional environment sensing device which is reliable.

It is a yet further object of the present invention to provide such a bifunctional environment sensing device which is easy to make.

It is a yet further object of the present invention to provide such a bifunctional environment sensing device which is simple.

It is a yet further object of the present invention to provide such a bifunctional environment sensing device which is compact.

It is a yet further object of the present invention to provide such a bifunctional environment sensing device which is cheap to make.

According to the most general aspect of the present invention, these and other objects are accomplished by an environment sensor comprising: (a) an insulating base board; (b) a first electrode made of a material which can provide an electrical indication of the value of a first physical quantity, formed on said insulating base board; (c) a second electrode formed of electrically conducting material and formed on said insulating base board; and (d) a mass of metal oxide semiconductor material which can provide an electrical indication of the value of a second physical quantity, layered on said base board over said first and second electrodes.

According to such a structure, the first electrode by itself constitutes a sensor which can sense the value of said first physical quantity, while the first and second electrodes together with the mass of metal oxide semiconductor material constitute a sensor which can sense the value of said second physical quantity. Accordingly, there is constituted an environment sensing device which is capable of sensing the values of two physical quantities at the same time, and which is thus capable of simultaneously sensing the values of said two physical quantities, independently. Thus, this bifunctional environment sensing device has a high sensing accuracy, and is suitable for measuring the value of a first physical quantity and also for measuring the value of a second physical quantity the value of which is used for correcting said measurement made of said value of said first physical quantity. In particular, this bifunctional environment sensing device is capable of sensing the value of temperature along with the value of some other physical quantity, which may be relative humidity. And such a bifunctional environment sensing device is capable of providing an output temperature value which corresponds to the temperature of the humidity sensor substantially exactly, so that good temperature correction may be made for the output value provided by said humidity sensor. Further, this bifunctional environment sensing device is reliable, and is easy to make. Also, this bifunctional environment sensing device is simple, is compact, and is cheap to make.

Further, according to a more particular aspect of the present invention, these and other objects are more particularly and concretely accomplished by such an environment sensor as specified above, further comprising a first and a second terminal electrically coupled to parts of said first electrode which are remote from one another and a third terminal which is electrically coupled to said second electrode.

According to such a structure, especially supposing that said electrical indication of the value of said first physical quantity is the resistance between said first and said second terminal, and that said electrical indication of the value of said second physical quantity is the resistance between said first and said third terminal, then the obtaining of electrical signals from said environment sensor is easy and convenient.

Further, according to a yet more particular aspect of the present invention, these and other objects are yet more particularly and concretely accomplished by such an environment sensor as specified above, wherein said first electrode and said second electrode are of extended shapes whose perimeters are long and are closely approached to one another; and further said first electrode and said second electrode may be of convoluted shapes.

According to such a structure, the resistance of said first electrode is made to be relatively high, and also the resistance between said first and said second electrode provided by said mass of metal oxide semiconductor material is made to be relatively low. Since typically the resistance of such a first electrode which is to be used for indicating temperature tends to be quite low, it is desirable to raise it to be high in this manner; and similarly but conversely since typically the resistance of such a mass of metal oxide semiconductor material which is to be used for indicating humidity tends to be quite high, it is desirable to lower it in this manner. Accordingly, the electrical characteristics of the environment sensor are made to be convenient.

BRIEF DESCRIPTION OF THE DRAWINGS

The present invention will now be shown and described with reference to the preferred embodiment thereof, and with reference to the illustrative drawings. It should be clearly understood, however, that the description of the embodiment, and the drawings, are all of them given purely for the purposes of explanation and exemplification only, and are none of them intended to be limitative of the scope of the present invention in any way, since the scope of the present invention is to be defined solely by the legitimate and proper scope of the appended claims. In the drawings, like parts and spaces and so on are denoted by like reference symbols in the various figures thereof; in the description, spatial terms are to be everywhere understood in terms of the relevant figure; and:

DESCRIPTION OF THE PREFERRED EMBODIMENT

Figure 1:
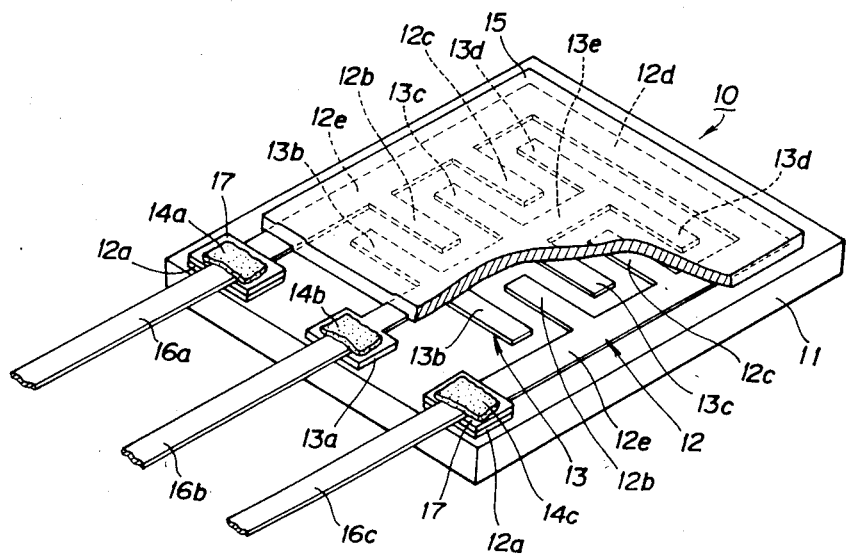
FIG. 1 is a perspective view of the preferred embodiment of the bifunctional environment sensor of the present invention, with a part thereof broken away.
Figure 2:
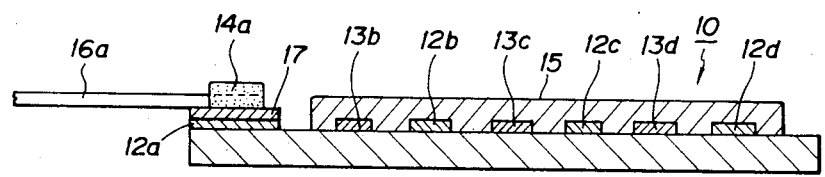
FIG. 2 is a sectional view of said preferred embodiment.

The present invention will now be described with reference to the preferred embodiment thereof, and with reference to the appended drawings. FIG. 1 is a perspective partly broken away view of this preferred embodiment 10 of the bifunctional environment sensor of the present invention, which is capable of sensing both ambient temperature and ambient humidity, which are taken as an exemplary pair of environmental quantities to be sensed; and FIG. 2 is a sectional view of this bifunctional environment sensor. In these figures, the reference numeral 11 denotes a rectangular insulating base board which may be made of a ceramic, and which is heat resistant and is shared between a temperature sensor subsystem and a humidity sensor subsystem, which will now be described. On this rectangular insulating base board 11 there are disposed two electrodes, a first electrode 12 and a second electrode 13. In fact, in this preferred embodiment of the present invention, these two electrodes 12 and 13 are formed on the base board 11 by a thick film technique making use of a screen printing method.

The first electrode 12 is shaped symmetrically, in this preferred embodiment, like three sides of a rectangle that extend along three sides of the rectangular insulating base board 11, with the side portions being denoted by the reference numerals 12e, 12e in FIG. 1, and with the end or middle portion denoted as 12d. Each of the side portions 12e terminates in an output tag 12a, and from each of these side portions 12e towards the central portion of the base board 11 there extend two extension pieces 12b and 12c. This first electrode 12 is made, in this preferred embodiment of the present invention, of an alloy of nickel, manganese, and cobalt (a Ni-Mn-Co alloy), which is a temperature sensitive material whose electrical resistance alters with its temperature. To the output tags 12a, 12a at the opposite ends of the first electrode 12 there are fixed pieces of electroconductive material 17 (see the sectional view of FIG. 2), and to these two pieces 17 of electroconductive material there are soldered, via pieces 14a and 14c of solder, output terminals 16a and 16c.

The second electrode 13 is shaped symmetrically, in this preferred embodiment, with a backbone portion 13e and with, on each side of this backbone portion, three extensions 13b, 13c, and 13d extending therefrom, so that the second electrode 13 as a whole is shaped like two letter E-shapes back to back, with the backs of the E-shapes extended downwards in FIG. 1 as the backbone portion 13e to terminate in an output tag 13a. The extensions 12b and 12c of the first electrode 12 lie in between these extensions 13b, 13c, and 13d of the second electrode 13 in an interlaced fashion. To the output tag 13a of the second electrode 13 there is directly soldered, via a piece of solder 14b, an output terminal 16b. This second electrode 13 is made of an electroconductive material, which, in this preferred embodiment, is a silver - palladium alloy (Ag-Pd).

Over the first and second electrodes 12 and 13 on the base board 11 there is formed a mass 15 of humidity sensitive material, which in this preferred embodiment of the present invention is made of lithium niobic acid (or LiNO₃), which is a per se known form of humidity sensitive metal oxide semiconductor material. Again, this layer or mass 15 of humidity sensitive material is formed on the base board 11 and the first and second electrodes 12 and 13 by making use of a screen printing method.

Figure 3:
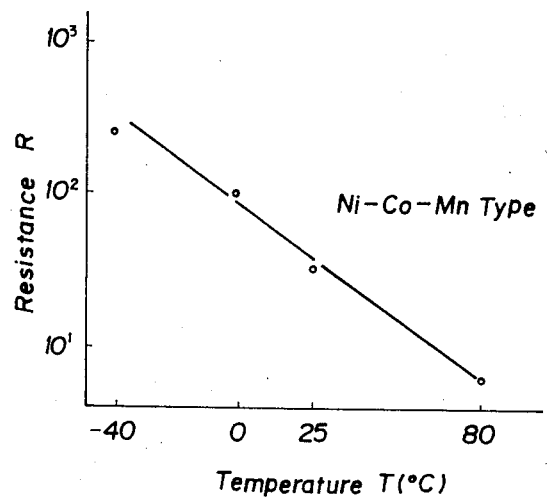
FIG. 3 is a graph in which temperature in degrees Celsius is shown on the horizontal axis and resistance in ohms is shown on the vertical axis on a logarithmic scale, showing the variation with respect to temperature of the electrical resistance of a nickel-cobalt-manganese temperature sensor element.

Thus, the bifunctional environment sensor 10 is mounted in a place where it is desired to detect and monitor both the temperature and the humidity, and electrical connection is made via lead wires or the like to the terminals 16a, 16b, and 16c, and these lead wires are used to link the sensor 10 to a monitoring device. Now, in this arrangement, the first electrode 12 by itself constitutes a temperature sensor subsystem, because, as the electrical resistance between the two terminals 16a and 16c connected to opposite ends of the first electrode 12 is measured, this electrical resistance alters with the temperature of the first electrode 12, as shown exemplarily in FIG. 3 of the drawings, which is a graph in which temperature in degrees Celsius of the first electrode 12 and of the sensor 10 as a whole is shown on the horizontal axis and the resistance in ohms of said first electrode 12 between its said terminals 16a and 16c is shown on the vertical axis on a logarithmic scale. Depending upon the sensing system, this resistance of the first electrode 12 may be manifested as a voltage (proportional to the resistance between the terminals 16a and 16c of the first electrode 12 if the current therethrough is kept constant), or may be manifested as a current amperage (proportional to the resistance between the terminals 16a and 16c of the first electrode 12 if the voltage applied thereto is kept constant).

Figure 4:
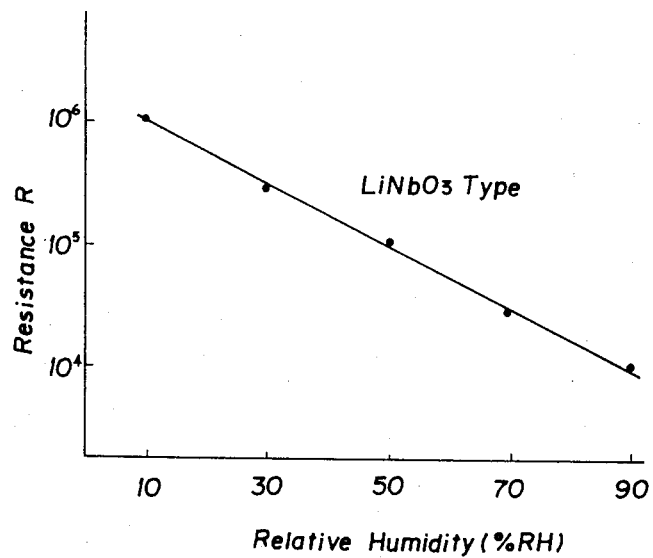
FIG. 4 is a graph in which relative humidity in percent is shown on the horizontal axis and resistance in ohms is shown on the vertical axis on a logarithmic scale, showing the variation with respect to relative humidity of the electrical resistance of a $LiNbO_3$ relative humidity sensor element.

Further, in this arrangement, the combination of the first electrode 12, the second electrode 13, and the mass 15 of humidity sensitive material constitutes a humidity sensor subsystem, because, as the electrical resistance between the two terminals 16a and 16b connected to the first electrode 12 and the second electrode 13 (or between the two terminals 16c and 16b—either pair will do) is measured, this electrical resistance alters with the ambient relative humidity, as shown exemplarily in FIG. 4 of the drawings, which is a graph in which relative humidity in percent is shown on the horizontal axis and resistance in ohms between the first electrode 12 and the second electrode 13 is shown on the vertical axis on a logarithmic scale. Again, depending upon the sensing system, this resistance between the first electrode 12 and the second electrode 13 may be manifested as a voltage (proportional to the resistance between the first electrode 12 and the second electrode 13 if the current between them is kept constant), or may be manifested as a current amperage (proportional to the resistance between the first electrode 12 and the second electrode 13 if the voltage applied between them is kept constant).

It will be noted that, because of the basic characteristics of this type of humidity sensitive substance like the lithium niobic acid (or LiNO₃) of which the mass 15 of humidity sensitive material is made, the resistance between the terminal 16a or 16c attached to the first electrode 12 and the terminal 16b attached to the second electrode 13 is of the order of $10^4$ to $10^6$ ohms, while on the other hand, again because of the basic characteristics of this type of temperature sensitive substance like the alloy of nickel, manganese, and cobalt (Ni-Mn-Co alloy) of which the first electrode 12 is made, the resistance between the terminal 16a or 16c attached to the first electrode 12 and the terminal 16b attached to the second electrode 13 is of the order of $10^1$ to $10^3$ ohms, i.e. is about three orders of magnitude lower than the aforementioned resistance between the terminal 16a or 16c attached to the first electrode 12 and the terminal 16b attached to the second electrode 13. This is why no substantial resistance signal representing ambient humidity is detected between the two end terminals 16a and 16c of the first electrode 12; the effect of conduction of electricity between the various parts of said first electrode 12 through the parallel resistance presented by the mass 15 of humidity sensitive material is quite negligible, by comparison with the much lower resistance between the two ends of said first electrode 12 itself. Similarly, this is why it makes no difference whether the terminal 16a or the terminal 16c of the first electrode 12 is used, when measuring the resistance between it and the terminal 16b of the second electrode 13 for determining an electrical signal representative of ambient humidity: the effect of the series resistance of said first terminal 12 is quite negligible, by comparison with the much higher resistance presented by the mass 15 of humidity sensitive material itself. The reason for forming the two electrodes 12 and 13 in the convoluted and convolved shapes shown, which have their own particular merits from the constructional and other points of view, so that said first electrode 12 and said second electrode 13 are of extended shapes whose perimeters are long and are closely approached to one another, is to decrease this resistance between the first and second electrodes 12 and 13 through the mass 15 of humidity sensitive material, by providing as short a serial path as possible therethrough, and as wide a parallel path therethrough as possible.

Thus, it is seen that the present bifunctional environment sensor is manufactured by a process which includes a step which is similar to the process of manufacturing a conventional type of metal oxide ceramic humidity detector. However, in such a conventional metal oxide ceramic humidity detector, it is usual to make both of the electrodes out of an alloy such as the nickel - palladium alloy used in the shown preferred embodiment of the present invention for the second electrode 13 only, or alternatively out of gold. But, in the present invention, because one of the electrodes is made of a material which is temperature sensitive, thereby it becomes possible to sense two physical quantities at the same time by using one and the same sensor. Indeed, according to the above described structure, the first electrode 12 by itself constitutes a sensor subsystem which can sense the value of a first physical quantity, which is temperature, while the first and second electrodes 12 and 13 together with the mass 15 of metal oxide semiconductor material constitute a sensor subsystem which can sense the value of a second physical quantity, which is humidity. Accordingly, there is constituted an environment sensing device which is capable of sensing the values of the given two physical quantities, temperature and humidity, at the same time, and which is capable of simultaneously sensing the values of said two physical quantities independently. Thus, this bifunctional environment sensing device has a high sensing accuracy, and is suitable for measuring the value of humidity and also for measuring a temperature value which is used for correcting said measurement made of said value of humidity. And such a bifunctional environment sensing device is capable of providing an output temperature value which corresponds to the temperature of the humidity sensor substantially exactly, since substantially the temperature sensor and the humidity sensor are physically one and the same device, so that good temperature correction may be made for the output value provided by the humidity sensor. Further, this bifunctional environment sensing device is reliable, since it is of unitary construction, and is easy to make, since per se known constructional techniques are used for its manufacture. Also, this bifunctional environment sensing device is simple, is compact, and is cheap to make.

Although the present invention has been shown and described with reference to the preferred embodiment thereof, and in terms of the illustrative drawings, it should not be considered as limited thereby. Various possible modifications, omissions, and alterations could be conceived of by one skilled in the art to the form and the content of any particular embodiment, without departing from the scope of the present invention. For example, although in the shown preferred embodiment the two physical quantities whose values were simultaneously measured by the bifunctional environment sensor were temperature and humidity, it could alternatively be chosen for the values of other pairs of physical quantities could be measured, such as temperature and density of a gas, or temperature and density of smog or smoke. In these cases, of course, a material would be required to be chosen for the mass of metal oxide semiconductor material covering the first and the second electrode on the base board which was capable of detecting gas density, or smog or smoke density, instead of the humidity detecting material used in the above described preferred embodiment. Other alterations could be conceived of. Therefore it is desired that the scope of the present invention, and of the protection sought to be granted by Letters Patent, should be defined not by any of the perhaps purely fortuitous details of the shown preferred embodiment, or of the drawings, but solely by the scope of the appended claims, which follow.

What is claimed is:
1. An environment sensor comprising:
   (a) an insulating base board;
   (b) a first electrode made of a material which can provide a first electrical indication of the value of a first physical quantity, formed on said insulating base board;
   (c) a second electrode formed of electrically conducting material and formed on said insulating base board; and
   (d) a mass of metal oxide semiconductor material which can provide a second electrical indication of the value of a second physical quantity essentially simultaneously with said first electrical indication, layered on said base board over said first and second electrodes.

2. An environment sensor according to claim 1, further comprising a first and a second terminal electrically coupled to parts of said first electrode which are remote from one another and a third terminal which is electrically coupled to said second electrode.

3. An environment sensor according to claim 2, wherein said electrical indication of the value of said first physical quantity is the resistance between said first and said second terminals.

4. An environment sensor according to claim 2, wherein said electrical indication of the value of said second physical quantity is the resistance between said first and said third terminals.

5. An environment sensor according to claim 3, wherein said electrical indication of the value of said second physical quantity is the resistance between said first and said third terminals.

6. An environment sensor according to claim 3, wherein said first electrode and said second electrode are formed as nonintersecting extended shapes whose perimeters closely approach one another.

7. An environment sensor according to claim 6, wherein said first electrode and said second electrode are of convoluted shapes.

8. An environment sensor according to claim 1, wherein said first physical quantity is temperature, and said first electrode is made of heat sensitive material.

9. An environment sensor according to claim 1, wherein said second physical quantity is humidity, and said mass of metal oxide semiconductor material is made of humidity sensitive material.

10. An environment sensor according to claim 3, wherein said first physical quantity is temperature, and said first electrode is made of a material whose resistance changes with temperature.

11. An environment sensor according to claim 3, wherein said second physical quantity is humidity, and said mass of metal oxide semiconductor material is made of a material whose resistance changes with humidity.

* * * * *